US010749355B2

(12) United States Patent
Grison

(10) Patent No.: US 10,749,355 B2
(45) Date of Patent: Aug. 18, 2020

(54) PHALLUS STORAGE CASE

(71) Applicant: Michell Roland Grison, Vitoria (CA)

(72) Inventor: Michell Roland Grison, Vitoria (CA)

(*) Notice: Subject to any disclaimer, the term of this patent is extended or adjusted under 35 U.S.C. 154(b) by 241 days.

(21) Appl. No.: 15/822,136

(22) Filed: Nov. 25, 2017

(65) Prior Publication Data
US 2019/0165585 A1 May 30, 2019

(51) Int. Cl.
| | |
|---|---|
| *H02J 7/00* | (2006.01) |
| *H02J 7/14* | (2006.01) |
| *B65D 25/10* | (2006.01) |
| *B65D 55/02* | (2006.01) |
| *A61L 2/10* | (2006.01) |
| *A61L 2/26* | (2006.01) |
| *B65D 25/28* | (2006.01) |
| *A61H 19/00* | (2006.01) |

(52) U.S. Cl.
CPC ............. *H02J 7/0027* (2013.01); *A61L 2/10* (2013.01); *A61L 2/26* (2013.01); *B65D 25/10* (2013.01); *B65D 25/28* (2013.01); *B65D 55/02* (2013.01); *A61H 19/44* (2013.01); *A61H 2201/1207* (2013.01); *A61L 2202/11* (2013.01)

(58) Field of Classification Search
USPC .................................. 320/111, 107, 108, 109
See application file for complete search history.

(56) References Cited

U.S. PATENT DOCUMENTS

| | | | | |
|---|---|---|---|---|
| 8,456,819 B1 * | 6/2013 | Smith | ................... | A47B 96/00 312/223.1 |
| 9,112,356 B2 * | 8/2015 | Cover | ................... | H02J 7/0003 |
| 10,225,734 B1 * | 3/2019 | Shipman | ............... | H04W 12/06 |
| 10,283,979 B1 * | 5/2019 | Grison | ...................... | H02J 7/02 |
| 10,439,408 B1 * | 10/2019 | Bastiyali | .................. | A61L 2/10 |
| 2007/0279002 A1 * | 12/2007 | Partovi | ................. | H02J 7/0027 320/115 |
| 2010/0213892 A1 * | 8/2010 | DeSanctis | ............ | H01R 25/006 320/107 |
| 2010/0231161 A1 * | 9/2010 | Brown | ...................... | B25H 3/02 320/101 |
| 2014/0125271 A1 * | 5/2014 | Wang | ..................... | H02J 7/0027 320/107 |
| 2014/0166900 A1 * | 6/2014 | Nelson | ...................... | A61L 2/10 250/455.11 |

(Continued)

*Primary Examiner* — Alexis B Pacheco
(74) *Attorney, Agent, or Firm* — Island IP Law; Stephen R. Burri

(57) ABSTRACT

A sex toy storage, charging, and sanitization device having a base with an internal electrical compartment; at least one vertical phallus support extending upwardly perpendicular to the base; an electrical outlet embedded in the base adjacent each of the at least one vertical phallus supports; a USB port embedded in the base adjacent each of the at least one vertical phallus supports; a string of ultraviolet 'C' frequency lights attached to the underside of the cover for sanitization; a supercharger for storing electrical power for recharging sex toys; an electric bar for recharging sex toys connected to the electrical outlet; a USB component for recharging sex toys connected to the USB port; an electrical cord for electrical connection to an external power source; and a cover, the device configured to resemble an antique sewing machine.

14 Claims, 5 Drawing Sheets

(56) References Cited

U.S. PATENT DOCUMENTS

| | | | |
|---|---|---|---|
| 2015/0137732 A1* | 5/2015 | Lai | H02J 7/025 |
| | | | 320/101 |
| 2015/0263547 A1* | 9/2015 | Browne | H02J 7/0027 |
| | | | 320/103 |
| 2016/0276852 A1* | 9/2016 | Roberts | H02J 7/0027 |
| 2017/0063114 A1* | 3/2017 | Briere | H02J 7/0044 |
| 2017/0256965 A1* | 9/2017 | Clark | H02J 7/0042 |
| 2017/0264117 A1* | 9/2017 | Deutsch | H02J 7/0044 |
| 2018/0085206 A1* | 3/2018 | Tsutsui | A61C 17/22 |
| 2018/0090951 A1* | 3/2018 | Watson | H02J 7/0027 |
| 2018/0102657 A1* | 4/2018 | Lin | H02J 7/0044 |
| 2018/0219392 A1* | 8/2018 | Dittrich | G04C 10/00 |
| 2019/0027944 A1* | 1/2019 | Grzybowski | H02J 7/0027 |

* cited by examiner

PHALLUS STORAGE CASE

FIELD OF THE INVENTION

The present invention relates to a sex toy accessory. In particular, the present invention relates to storage, charging and sanitizing of sex toys.

BACKGROUND OF THE INVENTION

It is known to provide a variety of sex toys, including phalluses, for entertainment purposes. Many such phalluses are electric and require batteries or are rechargeable.

It is desirable to provide a convenient, discrete apparatus for storage of phalluses. It is also desirable to provide means for discretely sanitizing and recharging the phalluses and batteries which may be used to operate the phalluses.

BRIEF DESCRIPTION OF THE DRAWINGS

A detailed description of the preferred embodiments is provided below by way of example only and with reference to the following drawings, in which.

Figure 1:
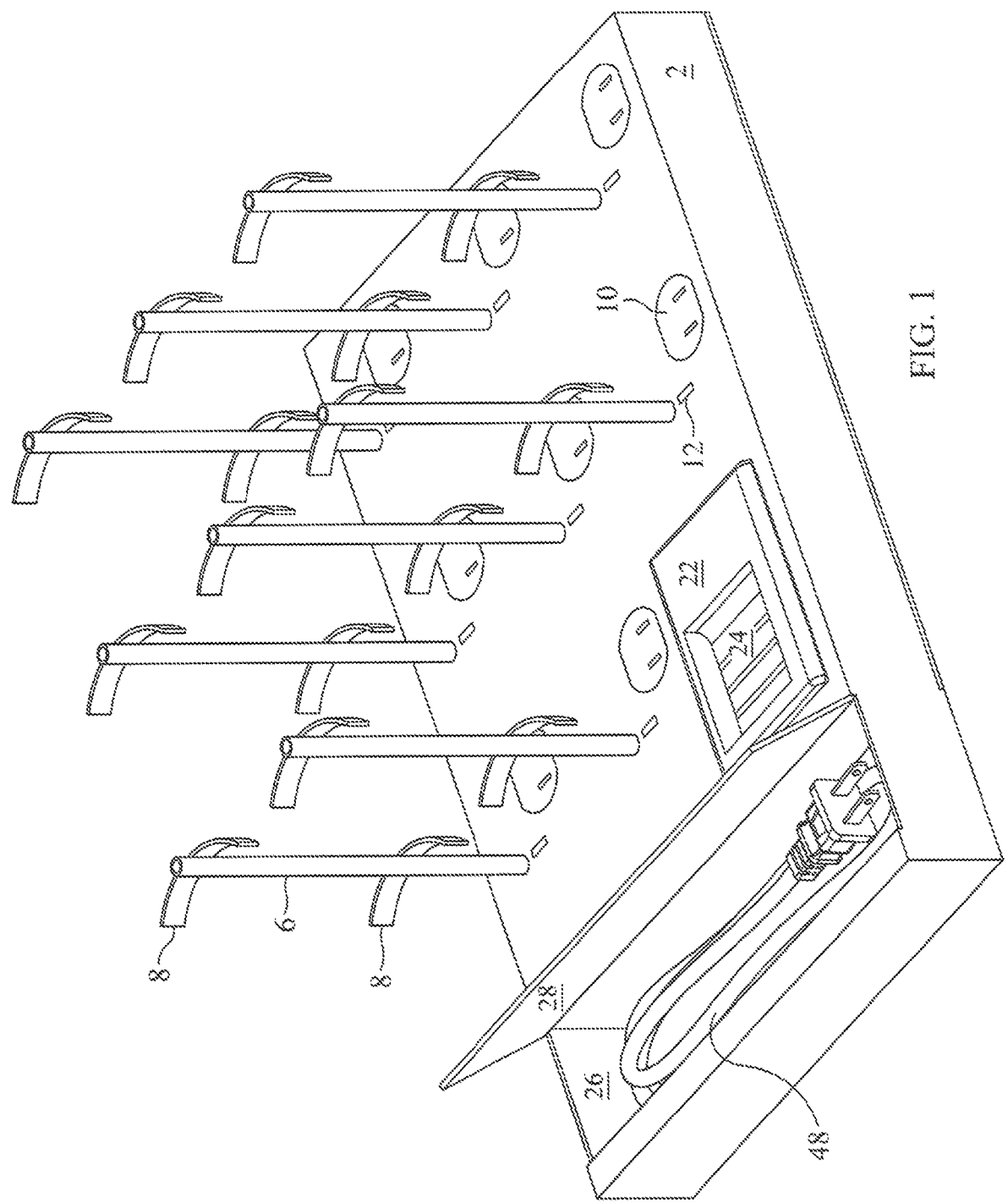
FIG. 1 is an upper perspective view of a preferred embodiment of the base of the present invention, with the cord compartment open.

In the drawings, several embodiments of the invention are illustrated by way of example. It is to be expressly understood that the description and drawings are only for the purpose of illustration and as an aid to understanding, and are not intended as a definition of the limits of the invention.

SUMMARY OF THE INVENTION

There is provided a sex toy storage and charging device comprising a base having an internal electrical compartment; at least one vertical phallus support extending upwardly perpendicular to the base; an electrical outlet embedded in the base adjacent each of the at least one vertical phallus supports; a USB port embedded in the base adjacent each of the at least one vertical phallus supports; a supercharger for storing electrical power for recharging sex toys; an electric bar for recharging sex toys connected to the electrical outlet; a USB component for recharging sex toys connected to the USB port; an electrical cord for electrical connection to an external power source; and a cover.

The device may include means for sanitization of sex toys stored therein using a string of ultraviolet 'C' frequency lights attached to the underside of the cover.

The sex toy device may have at least four vertical phallus supports, and preferably has eight vertical phallus supports. Each of the vertical phallus supports may include at least one arm support on one side of the vertical support, and preferably two spaced semi-circular arm supports on one side of each vertical phallus support.

There may be a rechargeable battery compartment and a cord compartment embedded in the upper side of the base, and an electrical compartment embedded in the lower side of the based, the cord compartment and electrical compartments preferably having rotatable covers.

The cover may include at least one external handle, and locking means for locking the cover to the base, preferably a tumbler lock. The sex toy device of the present invention is manufactured primarily of antimicrobial plastic.

The base and cover preferably resemble an antique sewing machine. The sex toy device may include a stand which resembles an antique sewing machine treadle.

DESCRIPTION OF THE INVENTION

As depicted in the drawings, the present invention comprises an apparatus for storage, charging, and sanitization of sex toys, in particular, phalluses. The apparatus comprises a base 2 and a cover 4.

As may be best seen in FIG. 1, the base further comprises a plurality of vertical phallus supports 6, each support having one or more semi-circular arms 8 along one side of each support. In the preferred embodiment, 8 supports are provided. Adjacent each support there is provided an electrical outlet 10 and a USB port 12 for insertion of a recharging plug or USB cord, respectively.

Figure 2:
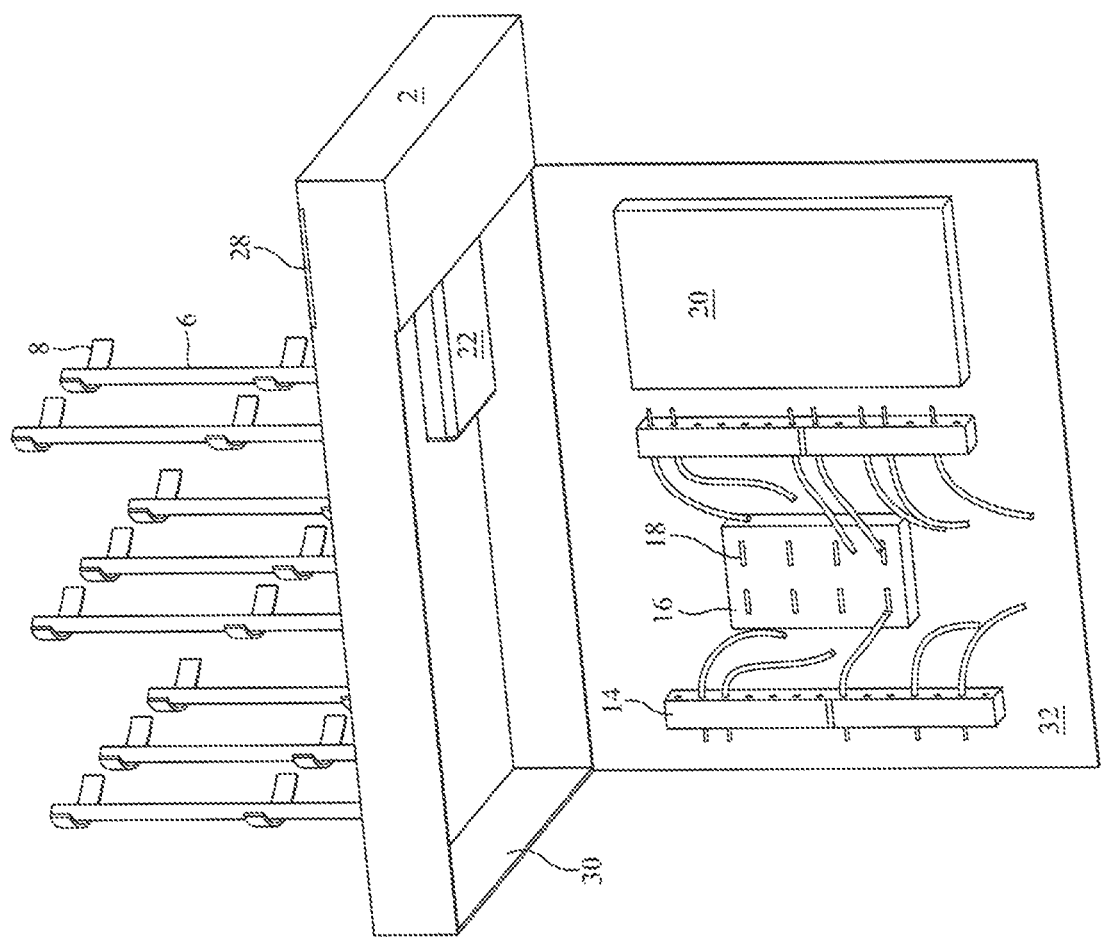
FIG. 2 is a lower perspective view of the preferred embodiment of the base of the present invention, with the electrical compartment open.
Figure 3:
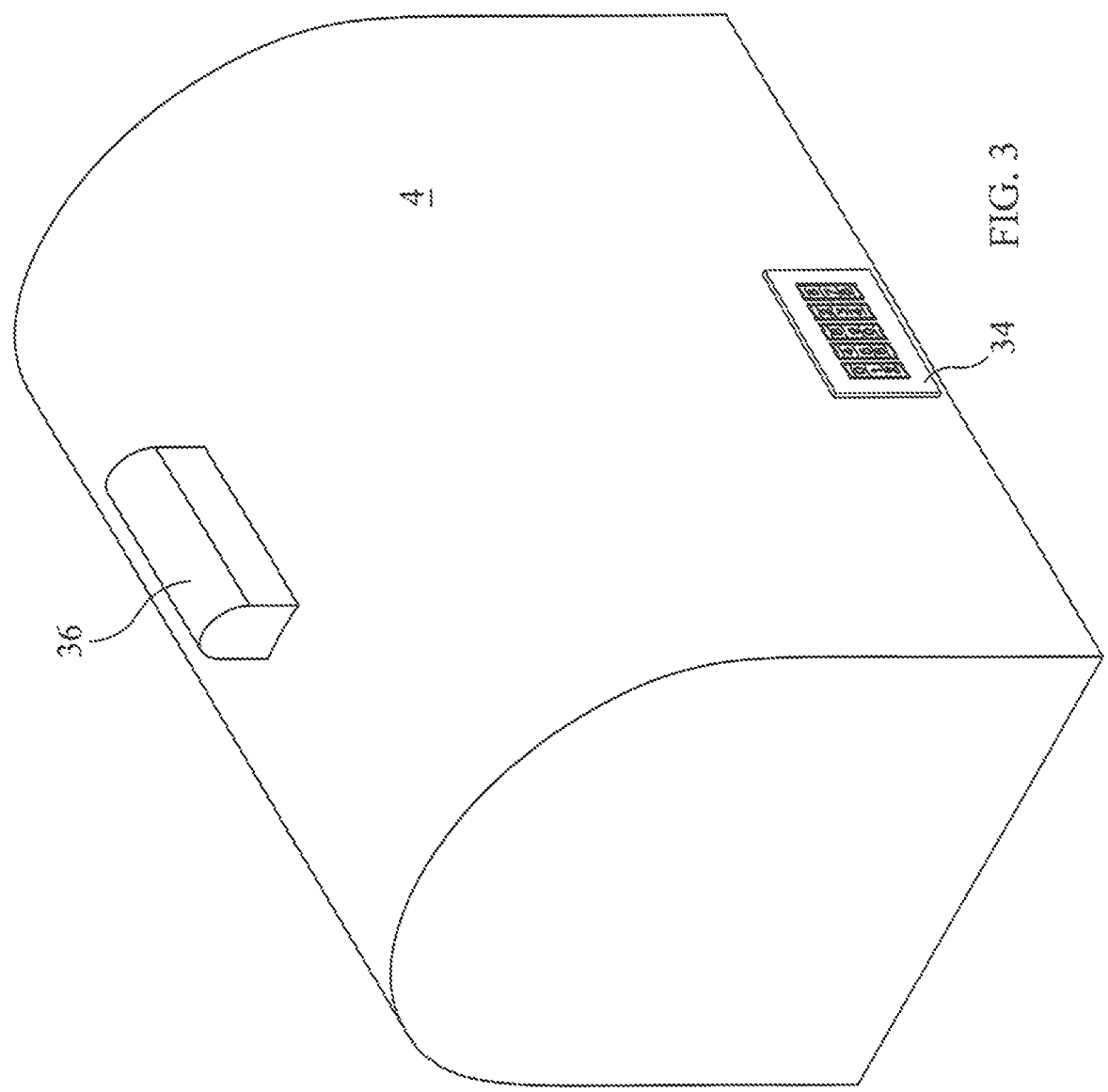
FIG. 3 is an upper perspective view of the cover of the present invention.
Figure 4:
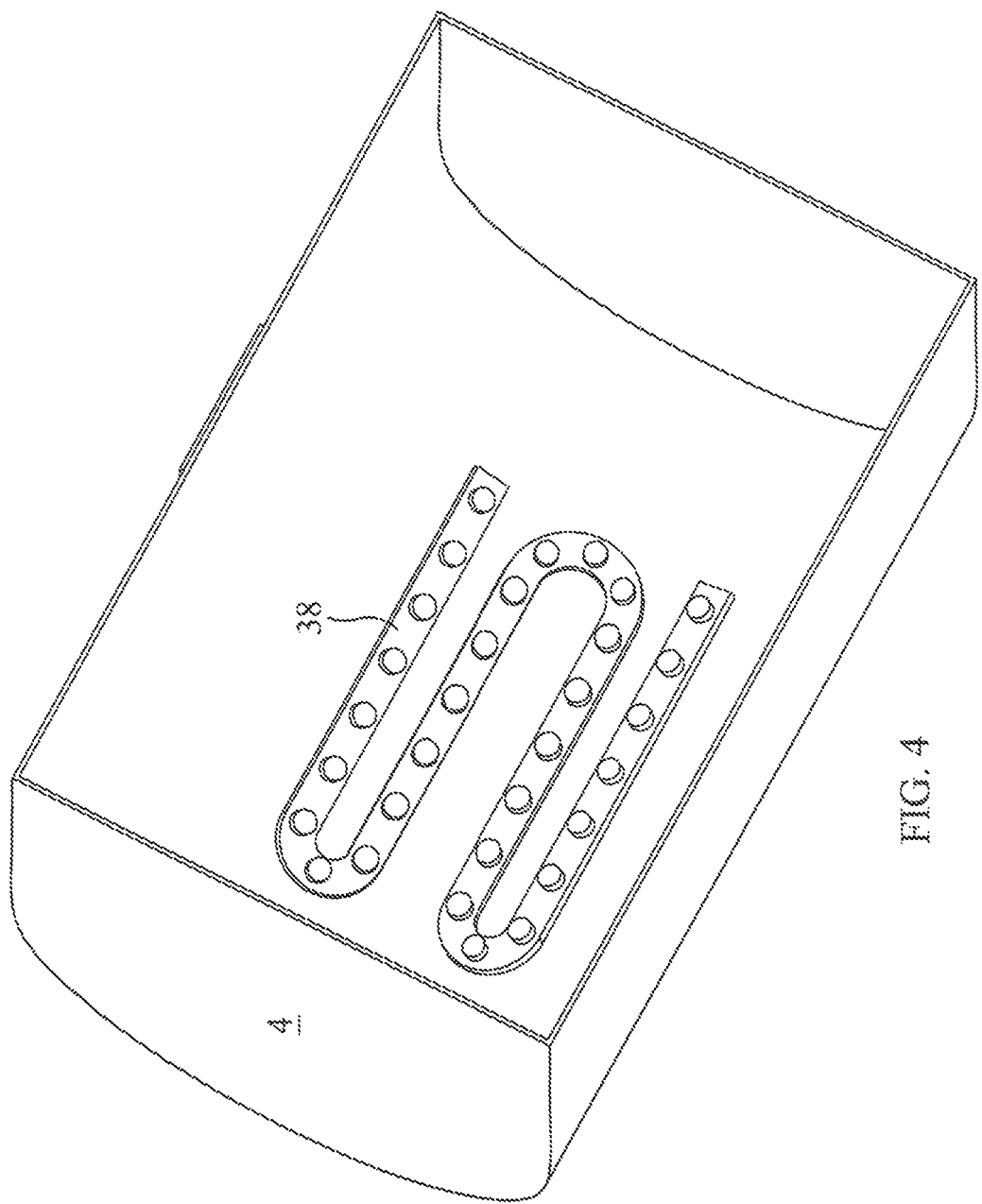
FIG. 4 is a lower perspective view of the cover of the present invention.
Figure 5:
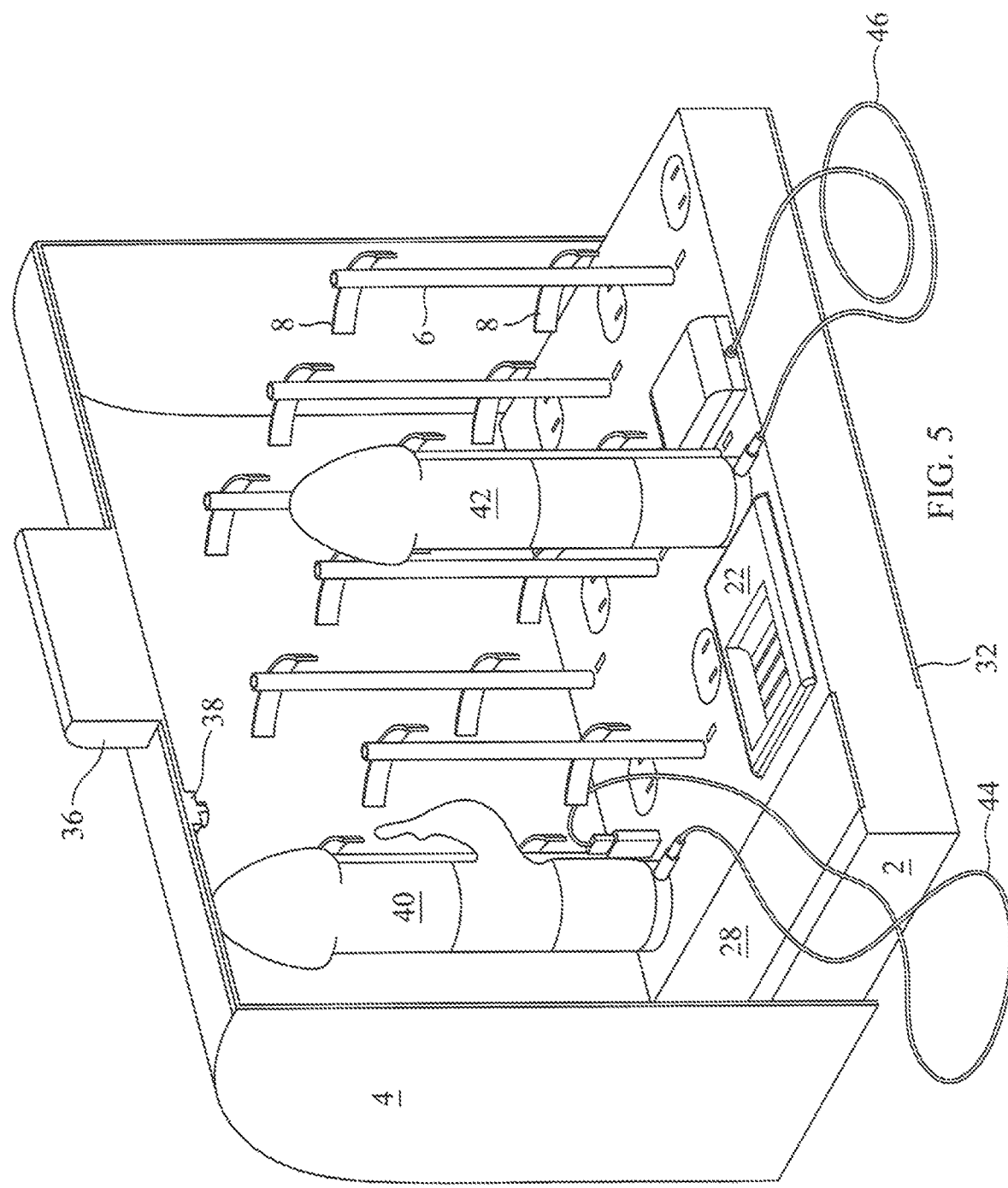
FIG. 5 is a cutaway view of a the base and cover of the invention, showing two sex toys mounted on the base.

With reference to FIG. 2, the base further comprises one or more electric bars 14 and a USB component 16 having 8 USB ports 18. A supercharger battery 20 is also stored in the electrical compartment. The electrical compartment 30 has a rotatable cover 32 to provide access to the electrical components.

On the upper side of the base, there is further provided a battery compartment 22 with slots 24 for recharging 4 "AA" type batteries. A cord compartment 26 with raiseable lid 28 is used for storage of an electrical cord 48 for connection of the apparatus to an AC electric power source.

Preferably, the base and cover of the invention are manufactured of antimicrobial plastic, but other materials are also possible.

The cover 4 of the invention preferably is in the shape of an antique sewing machine cover. This design will allow the invention to be placed in a home discretely by conveying the appearance of furniture, rather than intimate sexual devices. The cover is provided with a tumbler lock 34 and an upper handle 36. Other locking means are also possible within the scope of the invention. Other cover shapes are also possible within the scope of the invention. The invention may further comprise a stand resembling an antique sewing machine treadle.

A string of germicidal ultraviolet 'C' frequency ("UVC") lights 38 is disposed along the upper face of the inside of the cover to provide sanitizing UV radiation to the phalluses stored in the device. UVC light will destroy 99.9% of bacteria and viruses on the phalluses.

In operation, one or more phalluses 40, 42 are placed adjacent vertical phallus supports. Each USB charging cord 44 is inserted into the corresponding USB port, and each electrical charging cord 46 is inserted into the corresponding electric outlet. The cover is placed over the base and the apparatus is connected to an external power source. Each of the phalluses will be recharged while being stored in the device. In addition, the string of lights will sanitize each phallus, rendering it clean and ready for use.

Other uses for the device are also possible. For example, any small electrical device may be recharged in the device, including mobile phones, cameras, electric toothbrushes, shavers, laptops, and other devices. Also, any object may be sanitized in the device using the UVC light.

As many possible embodiments may be made of the invention without departing from the scope of the claims, it is to be understood that all matter herein set forth or shown in the accompanying drawings is to be interpreted as illustrative and not in a limiting sense.

It will be appreciated by those skilled in the art that other variations of the preferred embodiment may also be practised without departing from the scope of the invention.

The invention claimed is:

1. A sex toy storage and charging, device comprising:
   a. a base having an internal electrical compartment;
   b. at least one vertical phallus support extending upwardly perpendicular to the base;
   c. an electrical outlet embedded in the base adjacent each of the at least one vertical phallus supports;
   d, a USB port embedded in the base adjacent each of the at least one vertical phallus supports;
   e. a supercharger for storing electrical power for recharging sex toys;
   f. an electric bar for recharging sex toys connected to the electrical outlet;
   g. a USB component for recharging sex toys connected to the USB port;
   h. an electrical cord for electrical connection to an external power source;
   i. a cover; and
   j. means for sanitization of sex toys stored therein.

2. The sex toy device of claim 1, wherein the at least four vertical supports comprises eight vertical supports.

3. The sex toy device of claim 1, further comprising a rechargeable battery compartment embedded in the upper side of the base.

4. The sex toy device of claim 1, wherein each of the vertical phallus supports further includes at least one arm support on one side of the vertical support.

5. The sex toy device of claim 4, wherein the at least one arm support comprises two spaced semi-circular arm supports on one side of each vertical support.

6. The sex toy device of claim 1, further comprising a cord compartment embedded in the upper side of the base, the cord compartment having a cover.

7. The sex toy device of claim 1, further comprising an electrical compartment embedded in the lower side of the base, the electrical compartment having a cover.

8. The sex toy device of claim 1, wherein the means for sanitization of sex toys comprises a string a ultraviolet 'C' frequency lights attached to the underside of the Cover.

9. The sex toy device of claim 1, wherein the cover further at least one external handle.

10. The sex toy device of claim 1, wherein the cover further comprises means for locking the cover to the base.

11. The sex toy device of claim 10, wherein the locking means comprises a tumbler lock.

12. The sex toy device of claim 1, wherein the device is manufactured of antimicrobial plastic.

13. The sex toy of claim 1, wherein the base and cover, when assembled, resemble an antique sewing machine case.

14. The sex toy device of claim 13, further comprising a stand, wherein the stand resembles an antique sewing machine treadle.

* * * * *